United States Patent [19]
Benefiel et al.

[11] Patent Number: 5,594,249
[45] Date of Patent: Jan. 14, 1997

[54] SUBAMBIENT TEMPERATURE CONTROLLED CELL FOR INFRARED SPECTROSCOPIC ANALYSIS AND A METHOD FOR THE DETECTION OF PARAFFINIC HYDROCARBONS

[75] Inventors: David L. Benefiel, Oakland City; Louis R. Kessler; Alan J. Mitchell, both of Evansville, all of Ind.

[73] Assignee: Whirlpool Corporation, Benton Harbor, Mich.

[21] Appl. No.: 491,225

[22] Filed: Jun. 16, 1995

[51] Int. Cl.⁶ .......................... G01N 21/35; G01N 21/01
[52] U.S. Cl. .................. 250/339.03; 250/339.04; 250/339.07; 250/343
[58] Field of Search .............. 250/339.03, 339.04, 250/339.07, 343

[56] References Cited

U.S. PATENT DOCUMENTS

| | | | |
|---|---|---|---|
| 3,726,592 | 4/1973 | Corl et al. | 356/36 |
| 4,667,105 | 5/1987 | Miyatake et al. | |
| 4,749,276 | 6/1988 | Bragg et al. | 356/246 |
| 4,823,009 | 4/1989 | Biemann et al. | |
| 4,825,076 | 4/1989 | Shields | 250/343 |
| 4,942,134 | 7/1990 | Winefordner et al. | |
| 4,982,089 | 1/1991 | Johnson | 250/304 |
| 5,280,177 | 1/1994 | Bruno | 250/343 |

OTHER PUBLICATIONS

I. G. Voroshilov and B. S. Fantich, "Vessel for Investigating Infrared Spectra." *Instruments and Experimental Techniques*, Plenum Publishing Corporation (Dec. 1976) pp. 894–895. Translated from Pribory i Tekhnika Eksperimenta (USSR), vol. 19, No. 3, (May–Jun. 1976) pp. 247–248.

*Primary Examiner*—Constantine Hannaher
*Attorney, Agent, or Firm*—Hill, Steadman & Simpson

[57] ABSTRACT

A system and a method are provided for analyzing a small sample in a test chamber using infrared spectrophotometry. The invention is particularly applicable to analyzing a liquid sample in a test chamber by subjecting the liquid sample to infrared spectrophotometry and analyzing the infrared spectra of the subjected liquid sample. An evaporator is provided to cool the sample to sub-zero temperatures by forcing a refrigerant through the evaporator to cool the sample prior to testing.

20 Claims, 2 Drawing Sheets

SUBAMBIENT TEMPERATURE CONTROLLED CELL FOR INFRARED SPECTROSCOPIC ANALYSIS AND A METHOD FOR THE DETECTION OF PARAFFINIC HYDROCARBONS

BACKGROUND OF THE INVENTION

The present invention relates generally to a device for analyzing a small sample in a test chamber using infrared (IR) spectrophotometry. More specifically, the invention relates to a device and a method for detecting unwanted formations in liquid samples wherein the system maintains a dry atmosphere around the sample, and the sample is cooled to a desired temperature before and during scans.

Scientists have discovered that chlorofluorocarbons (CFC's) deplete ozone in the stratosphere. Ozone is the substance which protects us from the harmful effects of ultraviolet radiation. As a result, many governments have made a mandate to cease production of CFC's.

One of the most common refrigerants used today is CFC-12. Refrigeration system manufacturers throughout the industry have found HFC-134a to be a suitable alternative to CFC-12. In the initial phases of testing, it was soon discovered that certain contaminants in HFC-134a refrigeration systems would cause failures. Certain compounds are not soluble in HFC-134a at the low temperatures present in a refrigeration system. These substances tend to solidify in the small diameter of the expansion device. The reduced flow of refrigerant through the system results in a loss of the cooling effect. Only a few milligrams of deposit can cause a failure. The most common substance which is known to cause this failure is paraffin. It is a common component of many lubricants. These lubricants are used in the manufacture of refrigeration system components. Other hydrocarbons are also commonly used in these lubricants.

To eliminate paraffin from the refrigeration system, an analytical technique is needed to identify the paraffin in small samples. Paraffin is a straight chain hydrocarbon. Depending on its molecular weight, it can be solid liquid or even gaseous at room temperature. Common lubricants contain a mixture of solid and liquid paraffins. The solid paraffins are dissolved in the liquid paraffins resulting in a liquid product. When cooled, these paraffins will solidify. At a temperature of $-30°$ F., other hydrocarbons, such as naphthenic or polyalphaolefins, do not solidify. This is why they cause plugging in HFC-134a refrigeration systems. The IR spectrum of all three hydrocarbons is similar except for paraffin. A transition occurs in the IR spectrum when paraffins go from a liquid to a solid state. This is shown in FIG. 4. As illustrated, a singlet band at around 722 $cm^{-1}$ splits to form a doublet band. The doublet band generally occurs at 718 $cm^{-1}$ and 728 $cm^{-1}$. Thus, by cooling the sample and analyzing it by IR spectrophotometry, paraffin can be identified. Other analytical techniques are available; however, they require expensive equipment and lengthy test times.

One such known apparatus for analyzing a sample cell using infrared spectrophotometry is disclosed in U.S. Pat. No. 5,280,177. In the '177 patent, cooling of a sample to temperatures as low as $-45°$ C. is taught. To this end, a cool air passageway is provided adjacent a primary optical surface of a sample holder for directing a cool air stream across the primary optical surface. A vortex tube has a cool air outlet connected to the cool air passageway for supplying cool air to the passageway. The system disclosed in the '177 patent, however, is difficult to maintain very cool temperatures, and attaining of extreme temperature is often difficult within a short period of time. Further, moisture causing condensation contamination on a test disk and outside the chamber disk is a danger to the system described in the '177 patent.

A need, therefore, exists for an improved system and a method for analyzing a sample in a test chamber using infrared spectrophotometry.

SUMMARY OF THE INVENTION

The present invention relates to a system, device, and a method for analyzing a small sample in a test chamber and more particularly to a system using infrared spectrophotometry for analyzing a liquid sample in a test chamber by subjecting the liquid sample to infrared spectrophotometry. The system has a cooling means capable of subjecting the sample to sub-zero temperatures for testing the sample.

In an embodiment, the present invention provides a system for analyzing a sample in a test chamber using infrared spectrophotometry. The system has a sample holder in the test chamber capable of holding the sample to be analyzed. A refrigerant input line is capable of receiving a refrigerant to cool the sample in the sample holder. Receiving means is capable of receiving infrared transmissions from a source such that the transmissions are subjected on the sample in the sample holder.

In an embodiment, the refrigerant is carbon dioxide.

In an embodiment, the refrigerant line includes a coil surrounding the sample holder receiving the refrigerant in the coil.

In an embodiment, a metering valve is capable of regulating the refrigerant input into the refrigerant input line.

In an embodiment, a thermocouple wiring is capable of detecting a temperature in the test chamber.

In another embodiment of the present invention, a method is provided for analyzing a sample in a test chamber using infrared spectrophotometry. The method comprises the steps of: providing a sample in the test chamber; cooling the sample in the test chamber using a coil having a refrigerant added thereto; and subjecting the sample to infrared transmissions from a source.

In an embodiment, the method further comprises the step of providing an outlet for draining all wastes from the test chamber.

In an embodiment, the method further comprises the step of mounting a salt disk on the test chamber through which the infrared transmissions are transmitted.

In another embodiment of the present invention, a device is provided for analyzing a liquid sample in a test chamber by subjecting the liquid sample to infrared spectrophotometry and analyzing the infrared spectra of the subjected liquid sample. The device has a holder in the test chamber capable of receiving the liquid sample to be analyzed. Cooling means is capable of subjecting the sample to sub-zero temperatures for testing the sample by adding a refrigerant. A bracket is mounted on a wall of the test chamber and capable of holding a salt disk wherein infrared transmissions penetrate the salt disk and are directed to the sample.

In an embodiment, a nitrogen feeding means is capable of adding nitrogen to an interior of the test chamber.

It is, therefore, an advantage of the present invention to provide a system and a method for quickly analyzing a sample in a test chamber using infrared spectrophotometry.

Another advantage of the present invention is to provide a system and a method for efficiently cooling a sample in a test chamber subjected to analysis using infrared spectrophotometry.

Yet another advantage of the present invention is to provide a system and a method that implements a carbon dioxide evaporator coil wrapped around the sample disk to provide cooling by conduction from the $CO_2$ evaporator coil to the sample disk and sample.

A still further advantage of the present invention is to provide a system and a method that purges nitrogen into a sealed testing area allowing cold temperatures without causing moisture causing condensation contamination on the test disk and outside the chamber disk. Moisture damage to the disks is thereby prevented.

Additional features and advantages of the present invention are described in, and will be apparent from, the detailed description of the presently preferred embodiments and from the drawings.

DETAILED DESCRIPTION OF THE PREFERRED EMBODIMENTS

Figure 1:
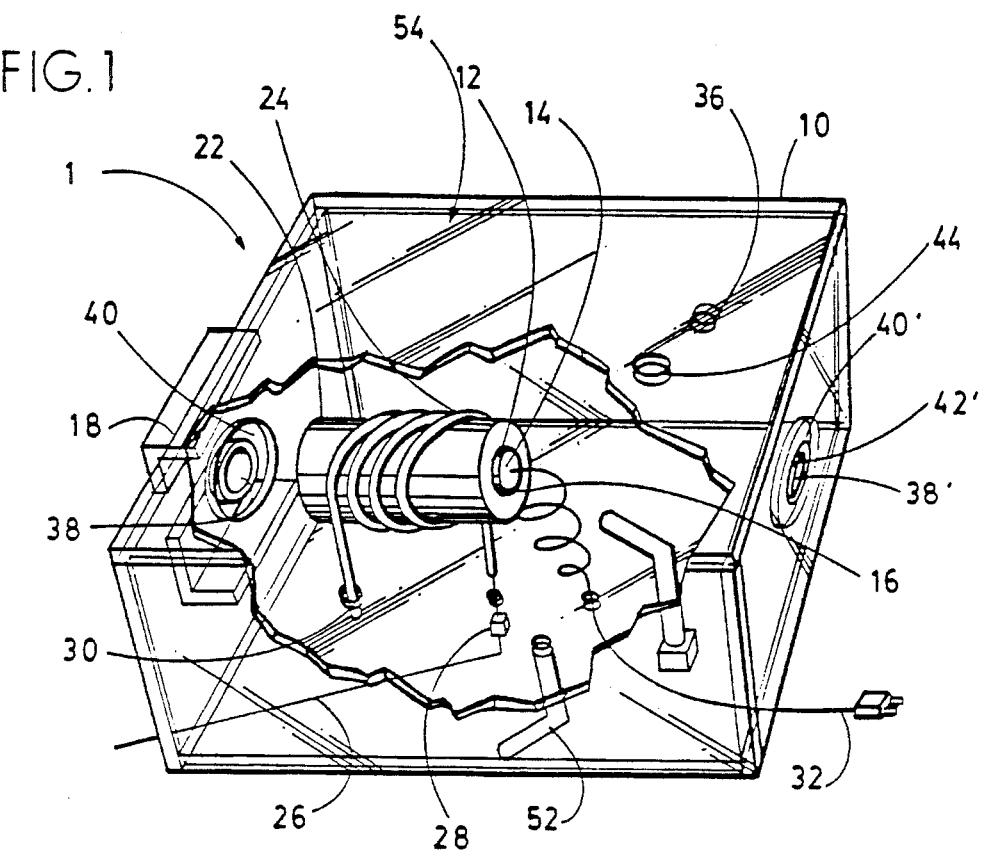
FIG. 1 is a perspective view of an embodiment of a test chamber illustrating internal components for analyzing a sample subjected to infrared spectrophotometry.

In FIG. 1, there is illustrated a device 1 for analyzing a sample therein. The device 1 includes a housing 10 preferably formed from 0.400-inch plexiglass. Within the housing 10 is a sample holder 12 capable of holding a sample disk 14 on which a sample can be analyzed. A metal plate 16 is provided in which the sample disk 14 is held.

A mounting block 18 is attached on a wall of the device 1 with an evaporator mounting bracket 20 securing an evaporator 22, preferably a carbon dioxide evaporator, to the mounting block 18. The evaporator 22 includes coils 24 therearound. The metal plate 16 is attached to the evaporator 22 holding the sample disk 14. Carbon dioxide ($CO_2$) may be added to the coils 24 through an inlet tube 26 and regulated by a metering valve 28. The metering valve 28 provides adjustment to a desired temperature, preferably −30° F. Preferably, a 1/16-inch stainless steel tubing is provided to the metering valve 28. A stainless steel outlet tube 30 exits the metering valve 28 and is then soldered to 1/8-inch copper tubing. The transition provides evaporation of $CO_2$ to provide cooling ability. For the coils 24, the 1/8-inch copper tubing continues to coil around one-inch copper tubing. The carbon dioxide exits from an outlet 30 and is vented away from test chamber 48. A thermocouple wire 32 is provided to penetrate a wall of the housing 10 and contacts the sample disk 14 to generate a sample test temperature.

Figure 2:
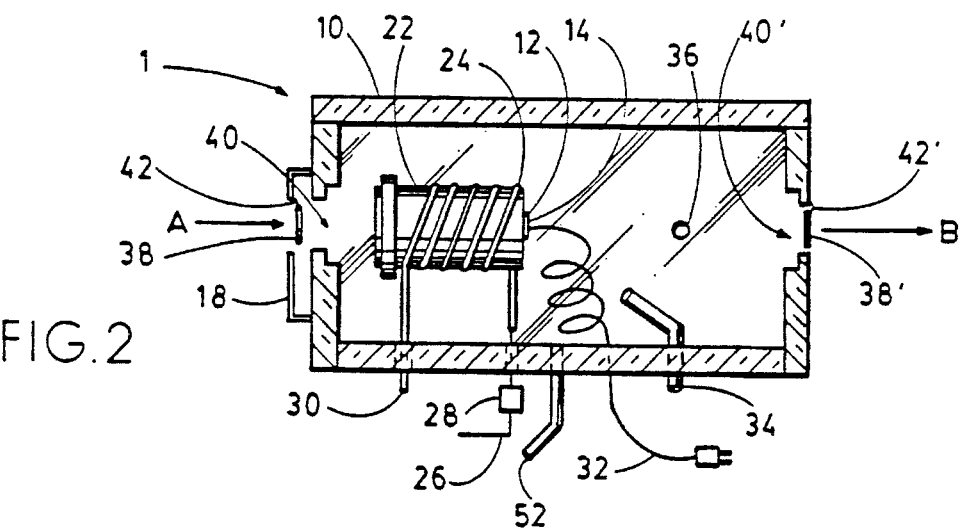
FIG. 2 is a cross-sectional view of an embodiment of a sample cell and test chamber of the present invention taken generally along the line II—II of FIG. 1.

Referring to FIGS. 1 and 2, dry nitrogen is purged into the housing 10 by an inlet tube 34 formed preferably from a 1/4-inch copper line bent at approximately a 45° angle. The inlet tube 34 penetrates into the housing 10, such that nitrogen, connected exterior to the housing 10 in a nitrogen tank (not shown) provides nitrogen into the housing 10. The nitrogen may exit through outlet tube 52 as shown in FIGS. 1 and 2. Preferably, all wastes exit this port formed by the outlet tube 52 as located on a bottom of the housing 10. As illustrated in FIG. 2, refrigerant, such as carbon dioxide, is added through the inlet tube 26 and is metered by the metering valve 28. The input of $CO_2$ to the coils 24 provides cooling of the sample disk 14, the temperature of which may be measured by the thermocouple wire 32.

A salt (KBr) disk 38 is centered in the mounting block 18 through which FT-IR scans can be run. Preferably, the salt disk 38 is substantially smaller than a hole 40 through which the scan is run. The salt disk 38 may be held by a strip of liquid adhesive 42. Similarly, a second salt disk 38' is attached at an opposite wall of the housing and held in place by a strip of liquid adhesive 42'. Again, a hole 40' is provided that is substantially larger than the salt disk 38'.

The arrow generally designated "A" in FIG. 2 indicates the direction of the IR scan through the salt disk 38 and the hole in the wall 40 leading to the sample disk 14 opposite the sample holder generally designated at 12. After the infrared transmission passes the salt disk 38 and the first wall of the housing 10, it continues through the sample disk 14 that preferably is held at −30° F. and then finally through the salt disk 38' after passing through the hole 40' and out of the housing 10 in the direction indicated by "B". The spectra of the sample exiting the housing 10 may then be analyzed to identify any impurities in the sample.

A sample may be introduced to the sample disk 14 through a sampling port 44. A plug may be placed in the sampling port 44 when sampling is not being performed. Preferably, a bent glass rod containing the sample at its end is provided to transfer the sample to the sample disk 14. In an embodiment, ester liquid samples are tested in the device for paraffin contained therein.

Figure 3:
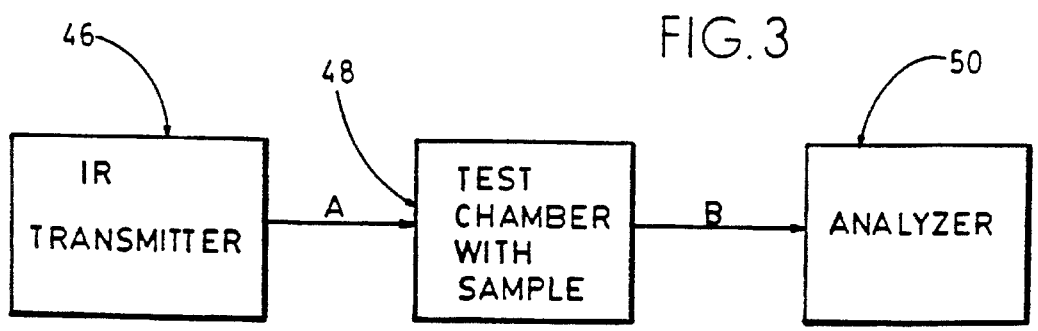
FIG. 3 illustrates a black box diagram of an embodiment of system components for analyzing a sample using infrared spectrophotometry.
Figure 4:
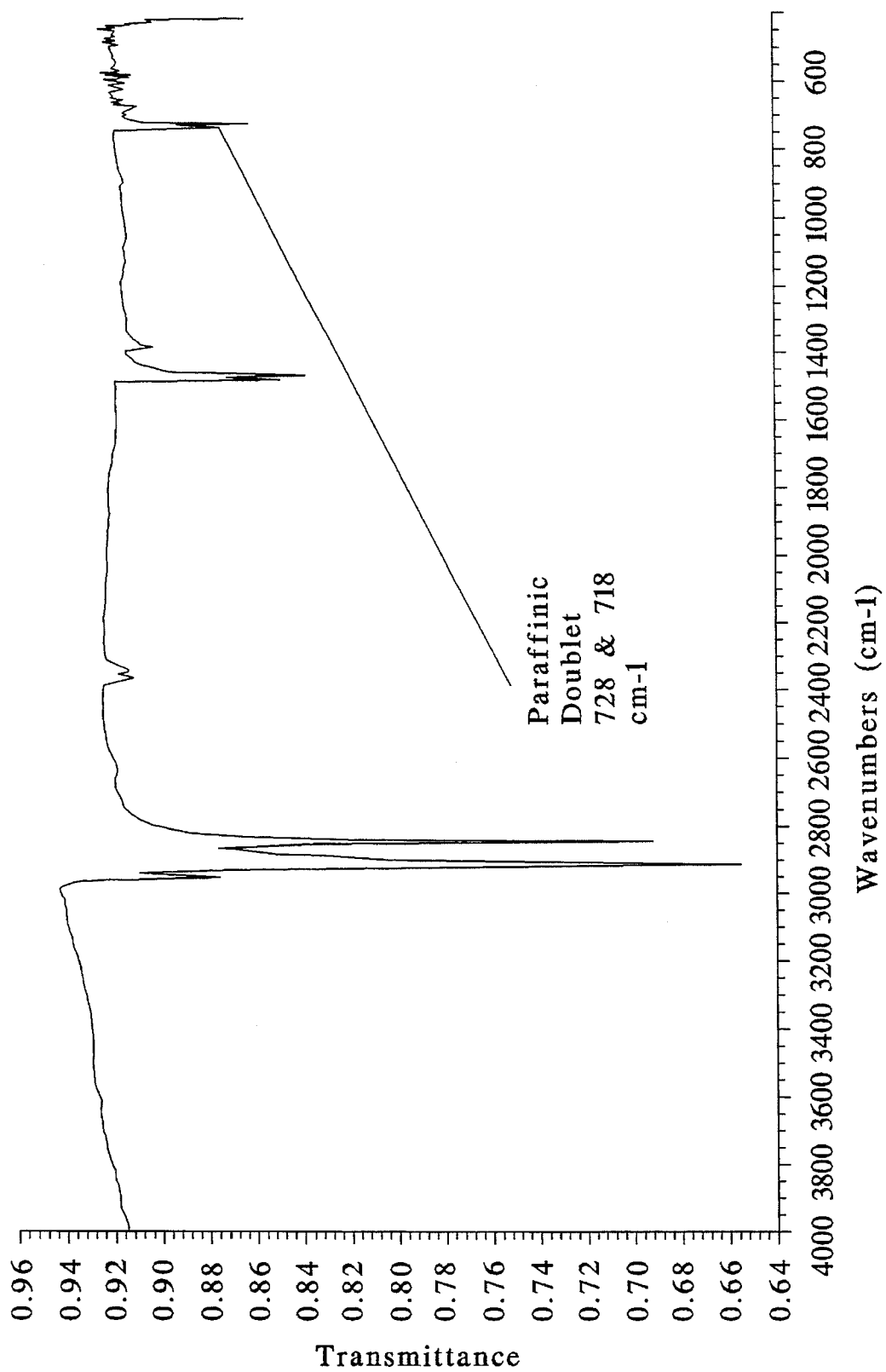
FIG. 4 illustrates a graph of an IR spectrum of a paraffin.

A plurality of FT-IR scans may be effected on the sample following insertion of the sample onto the sampling disk 14 through the sampling port 44. To this end, as illustrated in FIG. 3, an IR transmitter 46 transmits infrared transmissions to the test chamber 48 defined by the housing 10 in FIGS. 1 and 2. The IR transmission pass through the test sample on the sample disk 14 and the resultant spectrum may be analyzed by an analyzer as generally designated at 50. After testing of the sample is completed, the sample and disk 14 may be warmed to room temperature with the nitrogen. This prevents moisture damage to any of the disks. To this end, the $CO_2$ is first shut off, and the evaporator 22 is heated with nitrogen purged into the system for preferably three to five minutes, keeping flow directed on the sample disk 14. The sample disk 14 may then be cleaned with a suitable solvent, such as dichloromethane. All wastes may exit through a drain tube generally designated at 52 in FIG. 1. The drain tube 52 is preferably a 5/16-inch copper tube connected to stainless steel 0.028" providing adequate draining for the device 1.

To obtain best results, a lid 54 of the housing 10 is removed during and after solvent cleaning. The lid 54 may be lifted or removed as is conventionally known. The lid 54 provides access to the housing 10 and allows solvent vapors to be removed from the test area. Liquid solvents are then forced to go down the drain tube 52. If another sample test is required, the lid 54 may be replaced and the cooling step performed in order to provide a sub-zero environment for conducting the testing in the device 1. If no other sampling is required, the nitrogen is shut-off, and the carbon dioxide, nitrogen and thermocouple line may be disconnected. A valve 56 can be provided to control input from a nitrogen tank (not shown) into the housing 10 of the device 1.

As is apparent from the foregoing specification, the invention is susceptible of being embodied with various alterations and modifications which may differ particularly from those that have been described in the preceding specification and description. It should be understood that I wish to embody within the scope of the patent warranted hereon all such modifications as reasonably and properly come within the scope of my contribution to the art.

The embodiments of the invention in which an exclusive property or privilege is claimed are defined as follows:

1. A system for analyzing a sample in a test chamber using infrared spectrophotometry, the system comprising:
   a sample holder in the test chamber capable of holding the sample to be analyzed;
   a refrigerant input line capable of receiving a refrigerant to cool the sample in the sample holder; and
   receiving means freestanding in the test chamber and supported by the refrigerant input line wherein the receiving means supports the sample holder and is capable of receiving infrared transmissions from a source such that the transmissions are subjected through the receiving means to the sample in the sample holder.

2. The system of claim 1 wherein the refrigerant is carbon dioxide.

3. The system of claim 1 further comprising:
   input means capable of purging dry nitrogen into the test chamber.

4. The system of claim 1 wherein the refrigerant line includes a coil surrounding the sample holder receiving the refrigerant in the coil.

5. The system of claim 1 further comprising:
   a metering valve capable of regulating the refrigerant input into the refrigerant input line.

6. The system of claim 1 wherein the receiving means includes a mounting block capable of holding a salt disk and attached to the test chamber to receive the infrared transmissions through the salt disk.

7. The system of claim 1 further comprising:
   a thermocouple wiring capable of detecting a temperature in the test chamber.

8. A method for analyzing a sample in a test chamber using infrared spectrophotometry, the method comprising the steps of:
   providing a sample;
   providing an evaporator in the test chamber to which the sample is operatively attached;
   cooling the sample in the test chamber using a coil wrapped around the evaporator wherein the coil has a refrigerant added thereto; and
   subjecting the sample to infrared transmissions from a source wherein the source directs the transmissions through the evaporator onto the sample.

9. The method of claim 8 further comprising the step of:
   analyzing the infrared spectra of the subjected sample.

10. The method of claim 8 further comprising the step of:
    measuring temperature within the test chamber.

11. The method of claim 8 further comprising the step of:
    injecting dry nitrogen into the test chamber.

12. The method of claim 8 further comprising the step of:
    providing a sample holder within the test chamber capable of holding the sample therein.

13. The method of claim 8 further comprising the step of:
    providing an outlet for draining all wastes from the test chamber.

14. The method of claim 8 further comprising the step of:
    mounting a salt disk on the test chamber through which the infrared transmissions are transmitted.

15. A device for analyzing a liquid sample in a test chamber by subjecting the liquid sample to infrared spectrophotometry and analyzing the infrared spectra of the subjected liquid sample, the device comprising:
    a holder in the test chamber capable of receiving the liquid sample to be analyzed;
    cooling means capable of subjecting the sample to sub-zero temperatures for testing the sample by adding a refrigerant;
    a bracket mounted on a wall of the test chamber; and
    a salt disk held by the bracket mounted on the wall of the test chamber wherein infrared transmissions penetrate the salt disk and are directed to the sample.

16. The device of claim 15 further comprising:
    nitrogen feeding means capable of adding nitrogen to an interior of the test chamber.

17. The device of claim 15 wherein the refrigerant is carbon dioxide.

18. The device of claim 15 wherein the cooling means includes a coil constructed and arranged to surround an outside of the holder.

19. The device of claim 15 further comprising:
    a port constructed and arranged to receive the sample through the port for placement in the holder.

20. The device of claim 15 further comprising:
    a thermocouple wire constructed and arranged to detect temperature within the test chamber.

* * * * *